United States Patent [19]

Mailliet et al.

[11] Patent Number: 5,146,796
[45] Date of Patent: Sep. 15, 1992

[54] PROBE FOR TAKING GAS SAMPLES AND HEAT MEASUREMENTS ABOVE THE CHARGING SURFACE OF A SHAFT FURNACE

[75] Inventors: Pierre Mailliet, Howald; Emile Lonardi, Bascharage; Georges Wies, Dudelange, all of Luxembourg

[73] Assignee: Paul Wurth S.A., Luxembourg

[21] Appl. No.: 663,143

[22] Filed: Mar. 1, 1991

[30] Foreign Application Priority Data

Mar. 7, 1990 [LU] Luxembourg ............................. 87694

[51] Int. Cl.⁵ ................................................ G01N 1/22
[52] U.S. Cl. .................................. 73/866.5; 73/863.82;
73/864.73; 374/147; 374/148; 374/208
[58] Field of Search ............ 73/863.82, 863.58, 864.73,
73/866.5; 374/133, 139, 141, 147, 148, 157, 208

[56] References Cited

U.S. PATENT DOCUMENTS

| 2,260,794 | 10/1941 | Steudel | 73/863.82 |
| 2,934,959 | 5/1960 | Johnson | 73/863.82 |
| 3,643,508 | 2/1972 | Schneider | 73/866.5 |
| 3,888,123 | 6/1975 | Küntziger et al. | 73/863.11 |
| 4,061,036 | 12/1977 | Legille | 73/863.82 |

FOREIGN PATENT DOCUMENTS 0288341 5/1953 Switzerland .................. 73/863.82

Primary Examiner—Hezron E. Williams
Assistant Examiner—Rose M. Finley
Attorney, Agent, or Firm—Fishman, Dionne & Cantor

[57] ABSTRACT

The probe comprises a probe arm provided with a series of orifices for simultaneously taking gas samples and measuring the heat at different locations of the charging surface and penetrating through an opening in the furnace. This opening is surrounded by a support hoop integrally connected to the wall of the furnace and provided with two diametrically opposite outer journals on which are articulated two parallel arms supporting between them the probe arm. This arm can move about the center of the said hoop under the action of at least one actuator mounted between the said hoop and the outer end of the probe arm, the arm comprising a circular sliding surface moving, sealingly, over the inner surface of the said hoop.

12 Claims, 8 Drawing Sheets

PROBE FOR TAKING GAS SAMPLES AND HEAT MEASUREMENTS ABOVE THE CHARGING SURFACE OF A SHAFT FURNACE

TECHNICAL FIELD

The present invention relates to a probe for taking gas samples and heat measurements above the charging surface of a shaft furnace.

BACKGROUND OF THE INVENTION

Essentially two types of probe of the abovementioned type are known, namely those which are fixed and those which can be retracted through the wall of the furnace. Those which are fixed and cannot move above the charging surface have the disadvantage of disrupting the fall trajectory of the charging material and of being exposed to impacts with the latter, which results in very rapid wear. Those which can be displaced radially are introduced into the furnace between two charging cycles and are extracted again for the following charging cycle. These probes do not have the disadvantages of the fixed probes, but they do require means for displacing them, and means for sealing their passage through the wall of the furnace. Moreover, the handling they require constitutes a loss of time.

U.S. Pat. No. 4,061,036 describes an improved probe which pivots. The arm of this probe is fixed to a vertical rod passing through the oblique part of the wall of the head of the furnace and which comprises means for pivoting it about its vertical axis. Under the effect of this movement, the horizontal probe arm affects a sweeping movement over the charging surface. This probe has the advantage of being able to take measurements over its entire sweeping surface, whereas the other probes can take measurements only in a radial line. Furthermore, the probe arm can be displaced quickly into an averted position close to the wall of the furnace in which it does not disrupt the charging and is not exposed to the fall trajectory of the charging material. However, the upkeep of the probe, in particular the replacing of the thermocouples and the unplugging of the tubes for taking gas samples requires the whole probe to be disassembled, this disassembly being made all the more difficult by the fact that it must be performed vertically through the opening in the oblique part of the wall of the furnace.

All the probes known hitherto have the further disadvantage of not being able to be adapted to the charging profile, which can vary from one furnace to another. The consequence of this is that the heights at which the samples and heat measurements are taken vary from one measuring orifice to another, which can cause errors in interpreting the measurements.

SUMMARY OF THE INVENTION

The object of the present invention is to provide a novel probe of the type described in the preamble, which permits the thermocouples to be replaced easily, and the pipes for taking gas samples to be unplugged quickly without having to disassemble the probe, which makes it possible to adapt the inclination of the probe arm to the charging profile, and which permits the rapid displacement of the probe arm into an averted position without disrupting the charging process.

In order to achieve this objective, the present invention proposes a probe comprising a probe arm provided with a series of orifices for simultaneously taking gas samples and measuring the heat at different locations of the charging surface, said arm having a length greater than the radius of the furnace and being arranged so as to extend from the central region of the furnace to the outside of the latter, passing through an opening in the wall of the furnace. The probe is essentially characterized in that the said opening is surrounded by a support hoop integrally connected to the wall of the furnace and provided with two diametrically opposite outer journals on which are articulated two parallel arms supporting between them the probe arm, in that the said arm can move about the center of the said hoop under the action of at least one actuator mounted between the said hoop and the outer end of the probe arm, and in that the arm comprises a circular sliding surface moving, sealingly, over the inner surface of the said hoop.

The outer end of the probe arm is preferably carried by a suspension collar which is integrally connected to the two arms and on which the actuator is articulated.

According to a first preferred embodiment, the support hoop is a rolling-contact bearing block comprising a fixed ring integrally connected to the wall of the furnace, and a movable ring comprising the said journals and being able to revolve about the fixed ring under the action of a motor. This rotation enables the probe arm, when it occupies an angular position other than that corresponding to the axis of rotation, to move in precession, describing a surface corresponding to that of a hyperboloid. This enables the probe arm to be inclined parallel to the pouring slope in order to take measurements, and to be spaced apart laterally, as it moves in precession, into an averted position in order to be protected from the fall trajectory of the charging material.

Depending on the angle of the pouring slope, the rolling-contact bearing block can be oriented in different ways with respect to a diametral direction of the furnace. The block can be arranged in such a way that its axis of rotation is horizontal and diametral with respect to the furnace. The block can also be arranged in such a way that its axis is horizontal and forms an acute angle with the diametral axis of the furnace passing through the center of the rolling-contact bearing block.

The rolling-contact bearing block can also be inclined in such a way that its axis of rotation forms, in a vertical plane, an acute angle with the horizontal, being raised towards the center of the furnace.

According to another embodiment, the support hoop is a double hoop with the function of a universal joint comprising an outer hoop provided with the said pair of outer journals, and furthermore provided with a pair of inner journals arranged in a cross shape with the outer journals and pivoting on an inner hoop integrally connected to the wall of the furnace.

BRIEF DESCRIPTION OF THE DRAWINGS

Other features and characteristics will emerge from the detailed description of some embodiments given below, by way of illustration, with reference to the attached figures, in which.

DETAILED DESCRIPTION OF THE INVENTION

Figure 1A:
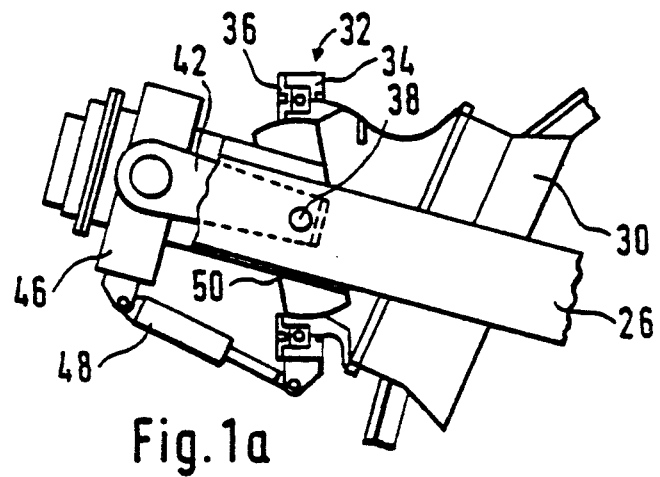
FIG. 1a shows the details of the suspension of the probe in vertical section.
Figure 1:
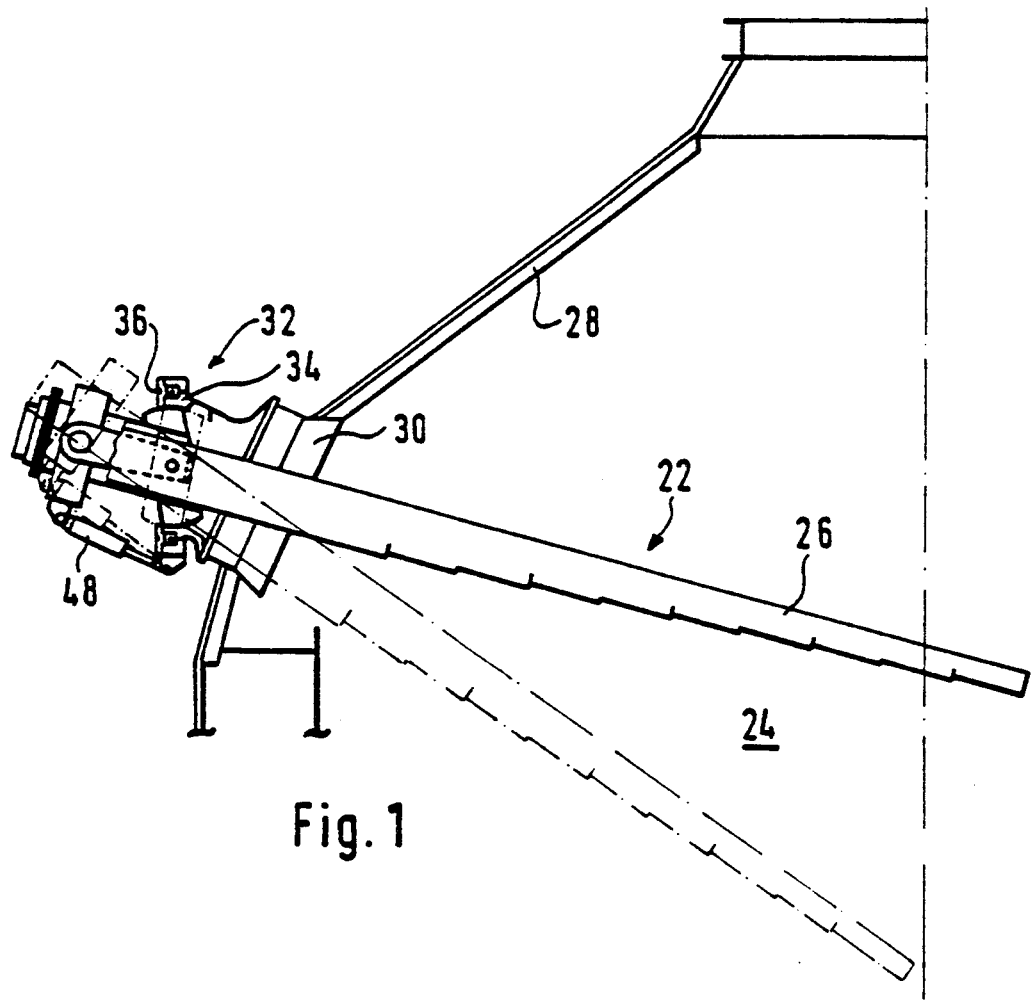
FIG. 1 shows diagrammatically a first embodiment of a probe according to the present invention, shown in two different inclined positions.
Figure 2:
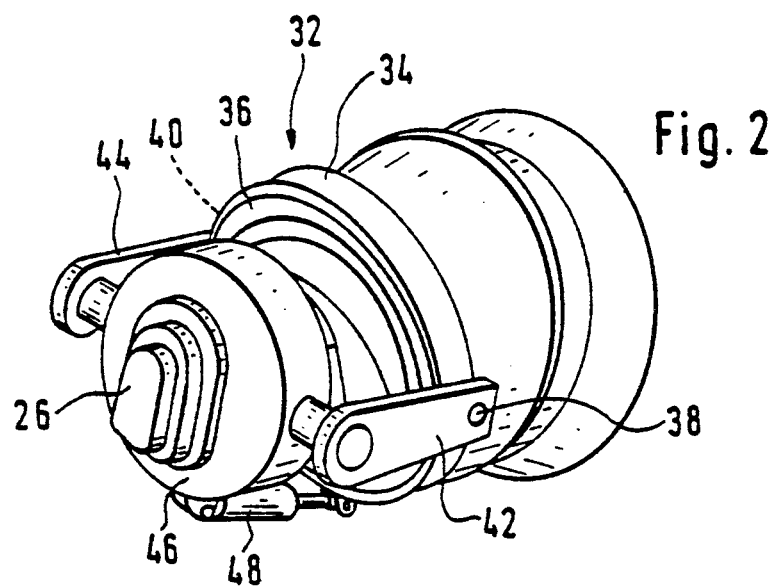
FIG. 2 shows a perspective of the outer part of the probe and of its suspension.

FIG. 1 shows a first embodiment of a probe 22 according to the present invention which is mounted above the charging surface of a blast furnace 24. This blast furnace is, more particularly, one which functions with a "V-shaped" charging profile, in other words with a conical pouring slope which rises from the center of the charging surface to the wall. The probe 22 essentially comprises a rectilinear probe arm 26 which is designed in order to permit access, in particular with a view to disassembly, to the thermocouples and to the mechanical tubes for taking samples, from outside the furnace without having to disassemble the probe arm 26.

According to the present invention, the probe comprises a suspension system for the arm 26 in order to permit it to be inclined, in the sampling/measuring position, in accordance with the gradient of the pouring slope, which is illustrated by the two different angular positions of the arm 26 shown in FIG. 1.

The probe arm 26 penetrates, by an opening 30, through the wall 28 of the furnace 24 and extends as far as the central region of the latter. The supporting of the arm 26 is ensured by a support hoop 32 integrally connected to the edge of the opening 30 and to the wall 28.

In the embodiment of FIG. 1, the support hoop 32 consists of a rolling-contact bearing block comprising a fixed ring 34 integrally connected to the edge of the opening 30, and a movable ring 36 which can revolve about the fixed ring 34 via known rolling-contact bearing means such as balls or rollers. This movable ring 36 is actuated by means, not shown, in order to enable it to rotate about the ring 34. To this end, it can be provided with a toothed ring forming a gearing with a driving pinion, not shown. The outer movable ring 36 comprises two diametrically opposite lateral journals 38 and 40 on which are articulated two arms 42 and 44 extending parallel on either side of the probe arm 26 and integrally connected to the latter via a suspension collar 46 provided around the outer part of the probe arm 26. A hydraulic actuator 48 mounted between the suspension collar 46 and the movable ring 36 enables the probe arm 26 to be tilted about the axis of the journals 38 and 40, as shown in FIG. 1, and the inclination of the probe arm 26 in the furnace thus to be modified.

The sealing between the inside of the furnace 24 and the outside is ensured by a ball-and-socket joint consisting, in this case, of a spherical segment 50 which is integrally connected to the probe arm 26 and the center of curvature of which corresponds to the center of rotation of the ring 36, which center is situated on the axis of the two journals 38 and 40. The inner surface of the fixed ring 34 of the block 32 is designed as a spherical sliding surface with the same center of curvature, so that the segment 50 can move sealingly over this sliding surface when the ring 36 rotates and when the probe arm 26 pivots about the axis of the journals 38 and 40. The sliding surface of the ring 34 can be provided, for this purpose, with a conventional gland packing. It should be noted that the segment 50 has solely a guiding and sealing function and performs no supporting function, this being performed entirely by the rolling-contact bearing block 32 in collaboration with the two arms 42, 44 carrying the probe arm 26.

Figure 3:
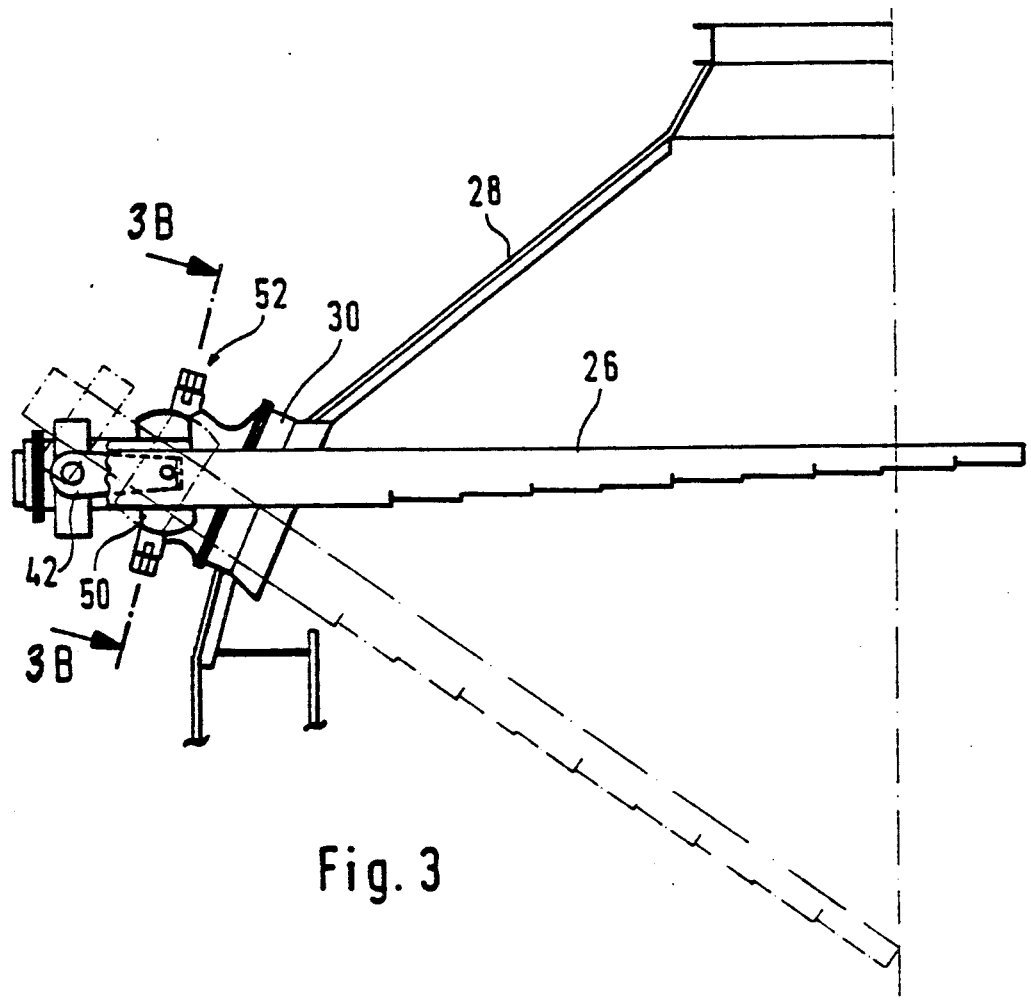
FIG. 3 shows a second embodiment according to the present invention.
Figure 3B:
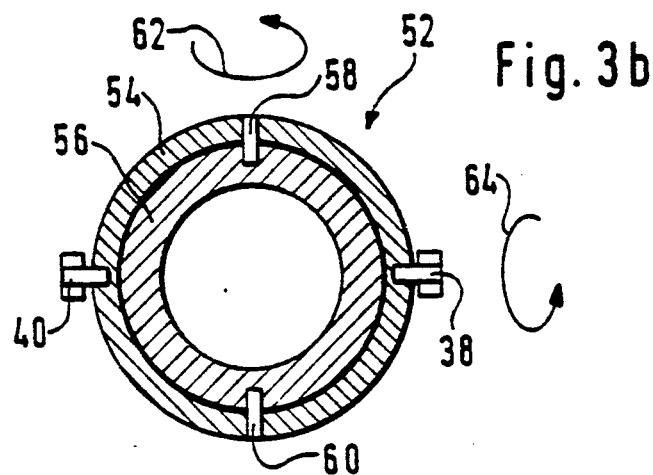
FIG. 3b shows a view along the plane of section B—B in FIG. 3.

FIG. 3 shows a second embodiment of the suspension for the probe arm 26. As in the first embodiment, the probe arm 26 is carried by two arms 42, 44 articulated on lateral journals 38 and 40 of a support hoop 52 integrally connected to the edge of the opening, the guidance and sealing likewise being ensured by a spherical segment 50 moving over the internal spherical sliding surface of the support hoop 52. However, in contrast to the embodiment according to FIG. 1, the support hoop 52 is not designed as a rolling-contact bearing block but as a universal joint. As shown in FIG. 3b, the support hoop consists of an outer hoop 54 provided with the journals 38 and 40, and of an inner hoop 56 which is fixed and which is integrally connected to the edge of the opening 30. The outer hoop 54 is connected to the inner hoop 56 via two journals 58, 60 arranged in a cross shape with the journals 38 and 40. The outer hoop can therefore pivot with respect to the inner hoop 56, about the axis of the journals 58 and 60, which is symbolized by the arrow 62. Independently of this, the probe arm 26 can pivot about the journals 38 and 40, which is symbolized by the arrow 64. These two pivoting movements are generated by hydraulic actuators, not shown, similar to the actuator 48 of FIG. 1. In order to enable the outer hoop 54 to pivot with respect to the inner hoop 56, their contact surfaces must have a spherical shape having as their center of curvature the point of intersection between the two axes of the four journals. This possibility of pivoting consequently enables the probe arm 26 to occupy any arbitrary inclination, horizontal or vertical, inside the furnace.

Figure 6:
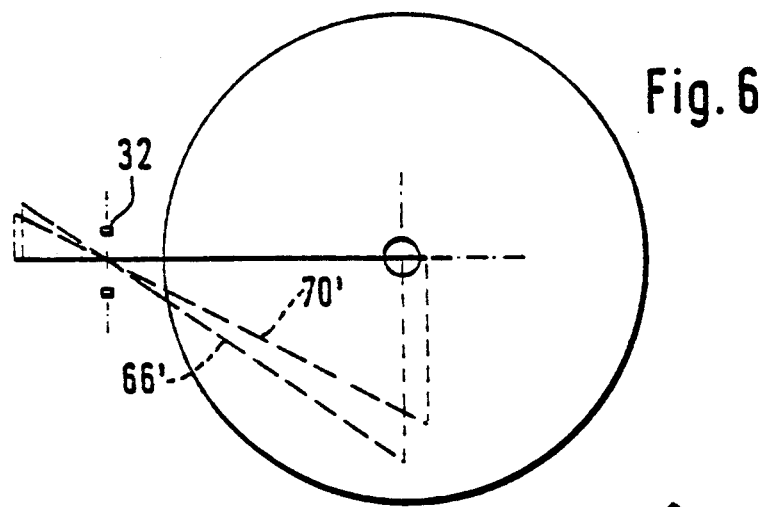
FIG. 6 shows diagrammatically the first method of operation in horizontal projection.
Figure 7:
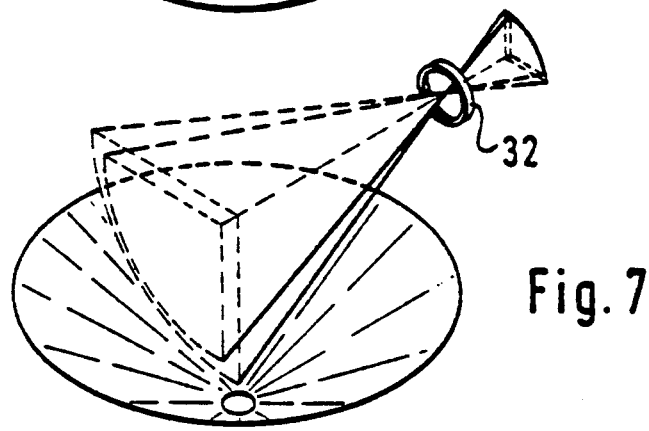
FIG. 7 shows the first method of operation in perspective.

A first mode of use of a probe for the embodiment according to FIG. 1 will now be described with reference to the two angular positions illustrated in FIG. 1. The position 66 illustrated in FIG. 4 corresponds to a charging profile with a very steep pouring slope. For sampling/measuring, the probe arm 26 is arranged parallel to the pouring slope by pivoting about its suspension journals 38 and 40 under the action of the actuator 48. At the end of the sampling/measuring, the probe arm 26 is displaced into an averted position in order to be protected from the trajectory of the charging material and from the great heat prevailing at the center of the furnace. To this end, the movable ring 36 of the support hoop 32 is rotated by a quarter of a revolution without modifying the angular position of the probe arm 26 with respect to its suspension journals. By virtue of this rotation of the ring 36 about its axis X, the probe arm 26 describes a movement of conical precession about the axis X corresponding to the surface of a hyperboloid, as shown in FIG. 7. The nose of the probe 26 describes, as shown in FIG. 5, a quarter of a circle 68 until the probe arm 26 is situated in a horizontal position corresponding to the averted position 66' illustrated in FIG. 6. The greater the inclination of the probe arm 26 in the sampling/measuring position according to FIG. 4, the closer to the wall is the averted position according to FIG. 6 since, as shown in FIG. 5, the radius of the circle 68 described by the nose of the probe 26 will increase in proportion to the degree of inclination of the arm.

Figure 4:
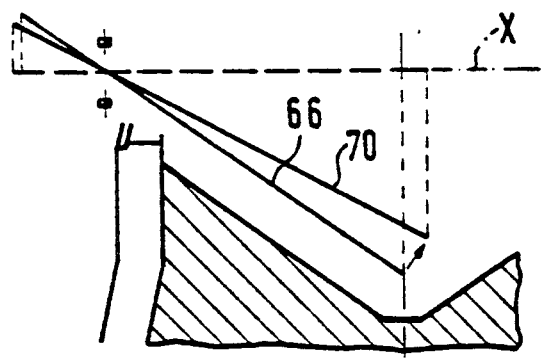
FIG. 4 shows diagrammatically a first method of operation in vertical projection.
Figure 5:
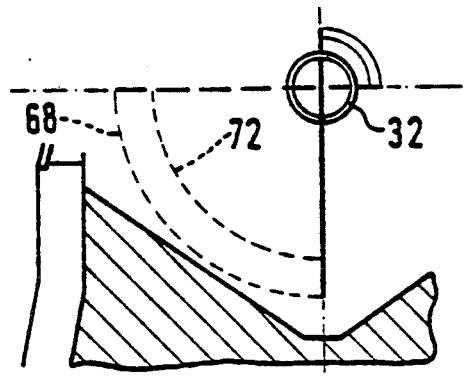
FIG. 5 shows diagrammatically the first method of operation in axial projection.

For sampling/measuring at a charging surface with a less steep pouring slope, the probe arm 26 can be raised, for example into the position illustrated by the reference 70 in FIG. 4. However, as shown in FIG. 5, the raising of the probe arm 26 into a less steep position, such as the position 70, reduces the radius of the circle 72 described by the nose of the probe arm when the latter is pivoted about the axis X. This means that, as confirmed in FIG. 6, the averted position 70' remains too far away from the wall of the furnace. However, this does not pose any problem since, once in the averted position 70', the probe arm 26 need only be pivoted horizontally about the axis of the journals 38, 40 by the actuator 48 in order to increase its angle with respect to the axis X, and thus to pivot the arm 26 until it is sufficiently close to the wall of the furnace, for example in the position 66' according to FIG. 6.

The embodiment according to FIG. 1, where pivoting and rotation of the probe arm 26 are possible, is more particularly designed for a shaft furnace which operates with different charging profiles, in other words with more or less steep pouring slopes. However, when a furnace operates with always the same pouring slope, there is no need to provide the possibility of the arm 26 pivoting about the journals 38 and 40. It will then be possible for the probe arm 26 to be integrally connected to the movable ring 36 with a given inclination with respect to the axis X corresponding to the angle of the pouring slope.

Indeed, as described with reference to FIGS. 4 to 7, when the pouring slope is steep and when the probe arm 26 occupies the position 66, no use is made of the possibility of the arm 26 pivoting about the journals 38 and 40 in order to displace the arm from a sampling/measuring position to an averted position and vice versa. On the other hand, when the probe arm 26 occupies a less steep position, such as that represented by 70 in FIG. 4, rotation of the arm 26 about the axis X alone is no longer sufficient to bring the probe into an averted position sufficiently close to the wall of the furnace, and recourse must be had to the pivoting of the arm 26 about these support journals 38 and 40 in order to increase the angle of inclination with respect to the axis X.

FIGS. 8 to 15 illustrate two methods of mounting the probe which enable this problem to be overcome and the probe to be displaced into an averted position outside the fall trajectory of the charging material, without there being any need for the probe arm to pivot.

Figure 8:
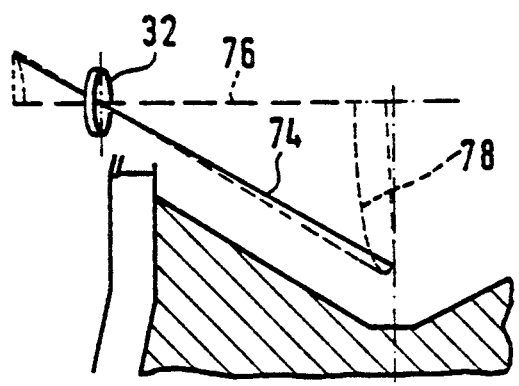
FIGS. 8 to 11 are diagrammatic views corresponding to FIGS. 4 to 7, and illustrate a second method of operation.
Figure 9:
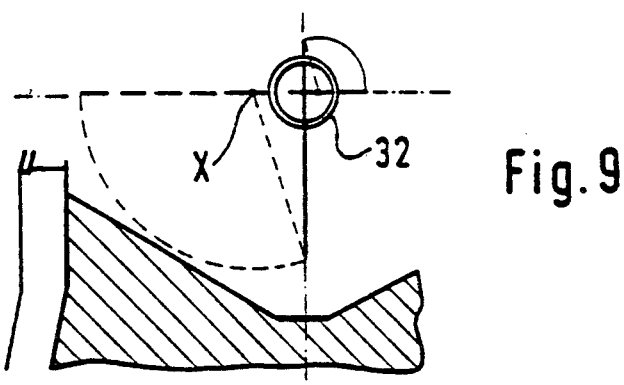
Figure 10:
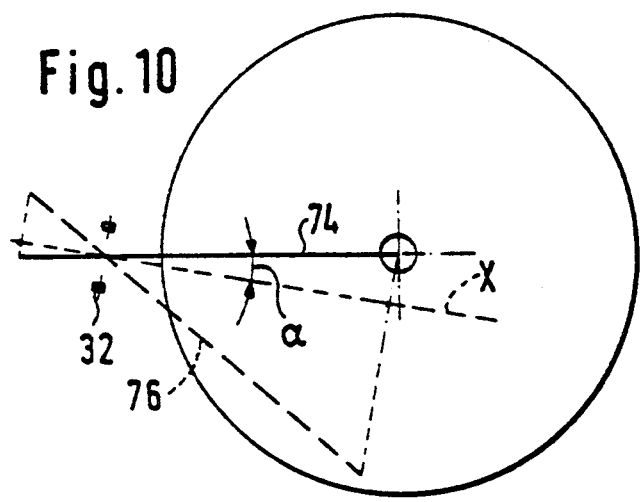
Figure 11:
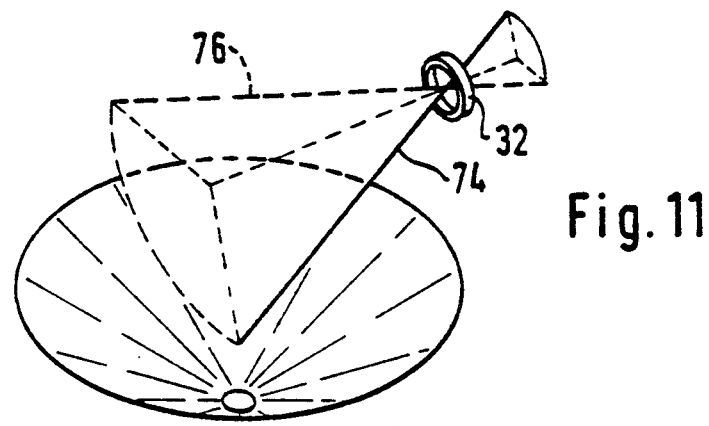

FIG. 8 shows the probe arm 26 in a position 74 at an angle of inclination corresponding substantially to that of the probe 70 in FIG. 4. In the embodiment of FIGS. 8 to 11, the pivoting provided in order to displace the probe arm according to FIG. 6 from the position 70' to the position 66' is replaced by a corresponding orientation of the support hoop 32 in such a way that the axis of rotation X forms, as shown in FIG. 10, an acute angle $\alpha$ with a vertical diametral plane. As a result, the nose of the probe arm 26 describes, when it pivots between the sampling/measuring position 74 and the averted position 76, an arc of a circle 78 (see FIG. 9) which is greater than 90°, the probe arm 26 still generating, as shown in FIG. 11, a surface of a hyperboloid. In this embodiment, the angle $\alpha$ will be smaller the steeper the pouring slope.

Figure 12:
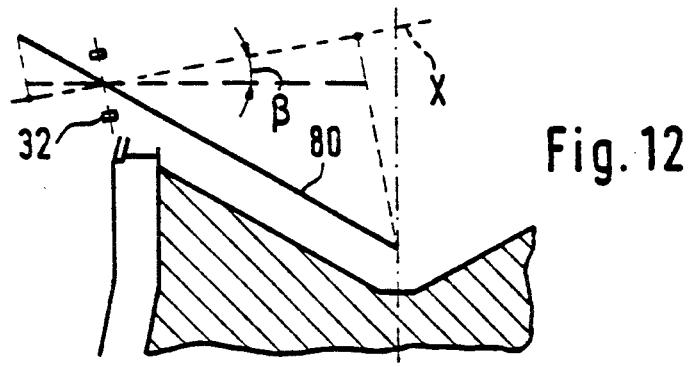
FIGS. 12 to 15 illustrate diagrammatically representations corresponding to FIGS. 4 to 7, and show a third method of operation.
Figure 13:
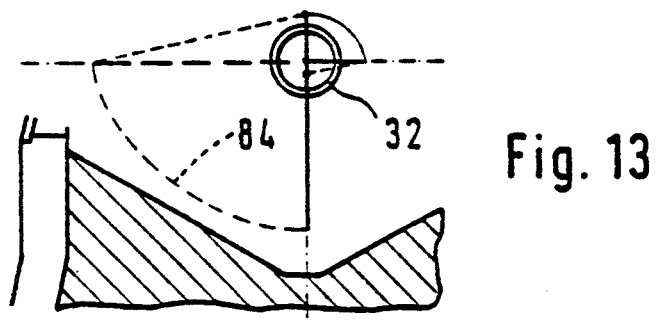
Figure 14:
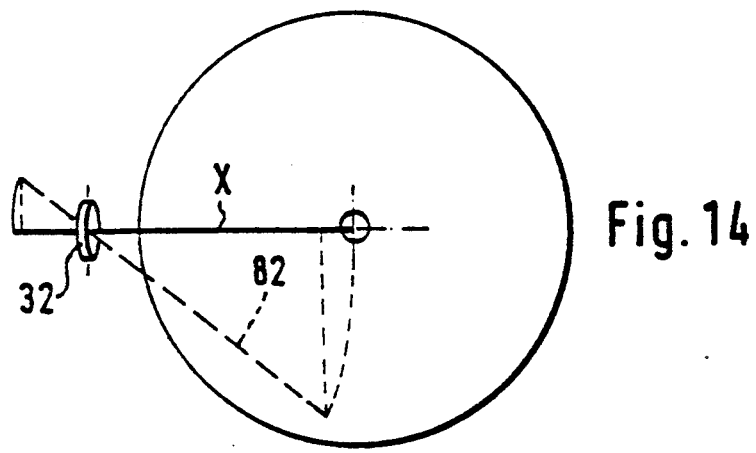
Figure 15:
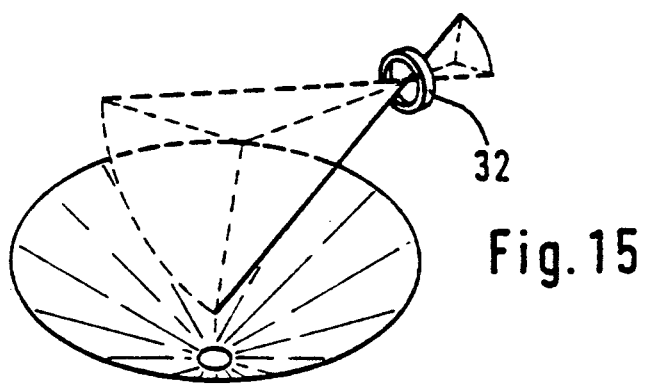
Figure 16:
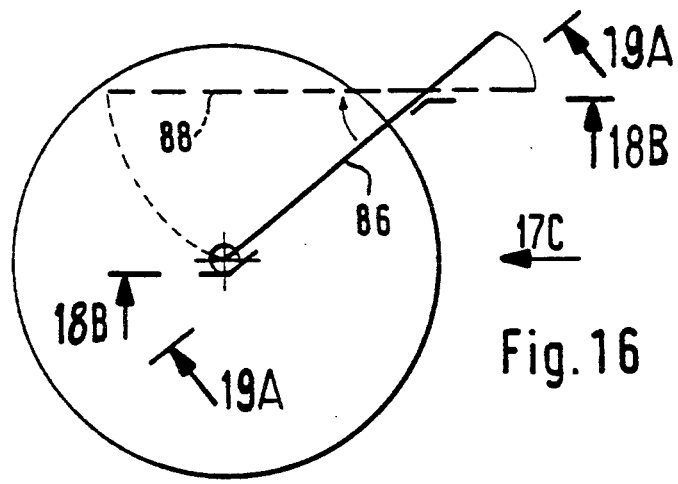
FIG. 16 illustrates diagrammatically, in horizontal projection, a fourth method of operation.
Figure 17:
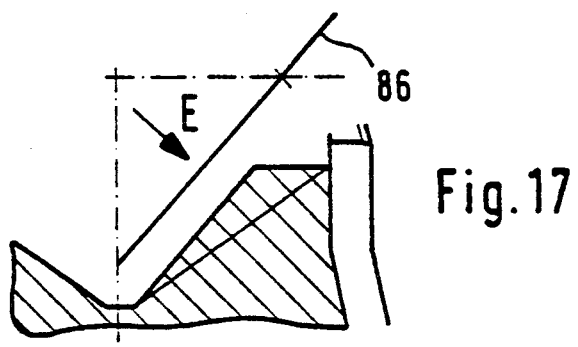
FIG. 17 shows diagrammatically a view in vertical projection in the direction C in FIG. 16.
Figure 18:
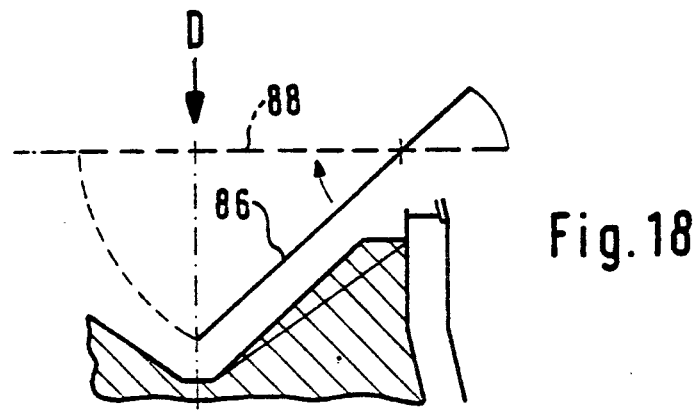
FIG. 18 illustrates diagrammatically a view in vertical projection in the direction B in FIG. 16.

A result similar to that of the arrangement according to FIGS. 8 to 11 can be obtained by the arrangement according to FIGS. 12 to 15. Indeed, according to FIG. 12, the position 80 of the probe arm in the sampling/measuring position corresponds substantially to the position 74 of FIG. 8 and, similarly, the averted position 82 corresponds substantially to the averted position 76 according to FIG. 10. However, as shown in FIG. 14, the axis of rotation X, contrary to FIG. 10, remains in the diametral plane but, as shown in FIG. 12, the support hoop 32 is oriented in such a way that its axis of rotation X forms in the diametral plane an angle $\beta$ with the horizontal when it is raised towards the center. The effect of this orientation of the axis X is clear from FIG. 13 which shows that the radius of the circle 84 described by the nose of the probe arm 26 is increased in proportion to the amplitude of the angle $\beta$, which means that, in the averted position 82 according to FIG. 14, the probe arm is further away from the vertical diametral plane. As in the embodiment of FIGS. 8 to 11, the angle $\beta$ may be reduced in proportion to the increase in the steepness of the pouring slope.

The embodiment of FIG. 3 requires no functional diagram to illustrate its maneuvering possibilities. Indeed, the cardan-type universal joint according to FIG. 3b enables the probe arm 26 to be placed in any arbitrary angular position irrespective of the inclination of the pouring slope.

When a furnace operates permanently with the same charging profile, it is even possible, following the example of the embodiment in FIG. 1, to simplify the embodiment of FIG. 3 by replacing the cardan-type universal joint with a suspension pivoting only about the journals 38 and 40, in other words to dispense with the journals 58 and 60 and to provide just one suspension hoop instead of two. FIGS. 16 to 20 are functional diagrams illustrating the movement of the probe arm 26 for such a simplified embodiment. These figures show the probe arm in the sampling/measuring position 86 and in the averted position 88 which is a horizontal position. In this simplified embodiment, the suspension of the probe arm 26 is designed in such a way that the axis of pivoting about the journals 38 and 40 is inclined with respect to the horizontal as a function of the steepness of the pouring slope. As a result, the probe arm 26 is displaced between the sampling/measuring position 86 and the averted position 88, and vice versa, by pivoting about the journals 38 and 40, sweeping an inclined plane as shown in the perspective view of FIG. 20.

Figure 19:
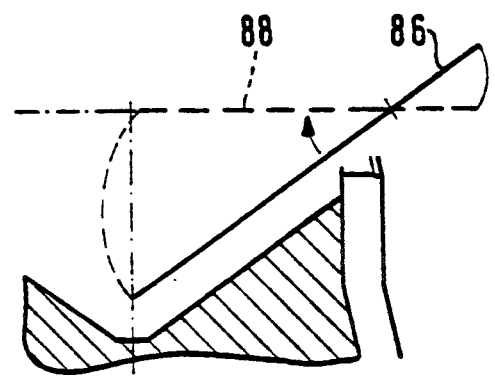
FIG. 19 shows diagrammatically a view in vertical projection in the direction A in FIG. 16.
Figure 20:
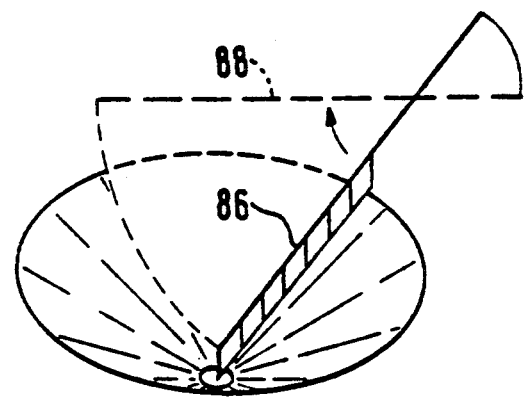
FIG. 20 shows a perspective view of the method of operation of FIG. 16.

The inclination of the probe arm in the sampling/measuring position, and the angle of the pouring slope, are illustrated in FIG. 19. These angles are greater in FIGS. 17 and 18 owing to the oblique views in directions C and D respectively.

While preferred embodiments have been shown and described, various modifications and substitutions may be made thereto without departing from the spirit and scope of the invention. Accordingly, it is to be understood that the present invention has been described by way of illustrations and not limitations.

What is claimed is:

1. A probe for taking gas samples and heat measurements above the charging surface of a shaft furnace, said shaft furnace having a furnace wall, comprising:
   a probe arm for inserting into the furnace through an opening in the furnace wall, said probe arm extending longitudinally from a first end, said first end to be disposed outside the furnace and including a circular sliding surface, to a tip, said tip to be disposed with said furnace, said arm defining a plurality of orifices for simultaneously taking gas samples and measuring heat at different locations above the charging surface;
   support hoop means surrounding said opening for pivotably and rotatably mounting said probe arm, said support means including:
      a pair of diametrically opposed articulated arms pivotably mounted on said probe arm,
      a pair of diametrically opposed outer journals for pivotably supporting said pair of articulated arms, and
      an inner surface for sealingly contacting the circular sliding surface of the probe arm; and
   actuator means mounted between the hoop means and the probe arm for moving said probe arm about the center of the support hoop means.

2. The probe of claim 1, wherein the probe arm further comprises a suspension collar rigidly secured to the first end of the probe arm, wherein the articulated arms and the actuator means are each pivotably connected to said suspension collar.

3. The probe of claim 1, wherein the hoop means further is a rolling contact bearing block and further comprises:
   a fixed ring rigidly secured to the furnace wall;
   a movable ring rotatably mounted within the fixed ring, wherein said outer journals are mounted on said movable ring; and
   means for rotating said movable ring relative to said fixed ring.

4. The probe of claim 3, wherein the rolling contact bearing block has an axis of rotation X and the axis of rotation X is oriented horizontally and diametrically with respect to the furnace wall.

5. The probe of claim 1, wherein the support hoop means is a universal joint and further comprise:
   an inner hoop rigidly secured to the furnace wall,
   an outer hoop surrounding said inner hoop, said outer journals being provided on said outer hoop, and
   a pair of diametrically opposed inner journals for pivotably securing said outer hoop to said inner hoop,
   wherein said diametrically opposed outer journals define a first line therebetween, said diametrically opposed inner journals define a second line therebetween and said first and second lines are oriented perpendicular to each other.

6. A probe for taking gas samples and heat measurements above the charging surface of a shaft furnace, said shaft furnace having a furnace wall, comprising:
   a probe arm for inserting into the furnace through an opening in the furnace wall, said arm defining a plurality of orifices for taking gas samples and measuring the heat at a plurality of different locations above the charging surface;
   a rolling contact bearing block means, surrounding the opening of the wall, for supporting the probe arm, said bearing block means comprising:
      a fixed ring rigidly secured to the furnace wall; and having a spherical inner surface;
      a movable ring rotatably mounted on said fixed ring;
      means for securing the probe arm to the movable ring; and
      spherical means, rigidly secured to the probe arm, for sealingly contacting the spherical inner surface of the fixed ring.

7. The probe of claim 6, wherein the rolling contact bearing block means has an axis of rotation X and the axis of rotation X is oriented horizontally and forms an acute angle $\alpha$ with a vertical diametral plane of the furnace wall which passes through the center of the bearing block.

8. The probe of claim 6, wherein the rolling contact bearing block means has an axis of rotation X and the block means is oriented so that the axis of rotation X forms in a vertical diametral plane an acute angle $\beta$ with the horizontal, bearing raised towards the center of the furnace.

9. A method for simultaneously taking gas samples and making heat measurements above the inclined charging surface of a shaft furnace, said shaft furnace being delimited laterally by a furnace wall, and said charging surface having a profile which rises from the center of said surface to said furnace wall, the method comprising:
   providing a probe assembly, said probe assembly comprising:
      a probe arm for inserting into the furnace through an opening in the furnace wall, said probe arm extending longitudinally from a first end, said first end to be disposed outside the furnace and including a circular sliding surface, to a tip, said tip to be disposed with said furnace, said arm defining a plurality of orifices for simultaneously taking gas samples and measuring heat at different locations above the charging surface;
      support hoop means surround said opening for pivotably and rotatably mounting said probe arm on said furnace wall, said support means including:
         a pair of diametrically opposed articulated arms pivotably mounted on said probe arm,
         a pair of diametrically opposed outer journals for pivotably supporting said pair of articulated arms, and
         an inner surface for sealingly contacting the circular sliding surface of the probe arm;
      actuator means mounted between the hoop means and the probe arm for moving said probe arm about the center of the support hoop means;
   pivoting the probe arm about the outer journals to bring the probe arm into a measuring position, said measuring position being generally parallel to the charging surface; and
   taking gas samples through said orifices of said probe arm while measuring temperature at different locations above the charging surface, while the probe arm is in the measuring position.

10. The method of claim 9, wherein the hoop means is a rolling contact bearing block and further comprises:
a fixed ring, rigidly secured to the furnace wall;
a movable ring rotatably mounted within the fixed ring; means for rotating said movable ring relative to said fixed ring; and
means for rotating said movable ring relative to said fixed ring, wherein said outer journals are mounted on said movable ring, further comprising the step of:
rotating the movable ring one quarter of a revolution relative to the fixed ring to bring the probe arm into an averted position, said averted position being close to the furnace wall, so that the probe arm is protected from a stream of additional charging material.

11. The method of claim 10, further comprising pivoting the probe arm about the outer journals from the averted position toward the furnace wall.

12. The method of claim 9, wherein the support hoop means is a universal joint and further comprises:
an inner hoop rigidly secured to the furnace wall,
an outer hoop surrounding said inner hoop, said outer journals being provided on said outer hoop, and
a pair of diametrically opposed inner journals for pivotably securing said outer hoop to said inner hoop,
wherein said diametrically opposed outer journals define a first line therebetween, said diametrically opposed inner journals define a second line therebetween and
said first and second lines are oriented perpendicular to each other further comprising the step of:
pivoting the probe arm about the inner and outer journals from said measuring position into an averted position, said averted position being situated above the charging surface close to the furnace wall; so that the probe arm is protected from a stream of additional charging material.

* * * * *